US009568487B2

(12) United States Patent
Cipolla

(10) Patent No.: US 9,568,487 B2
(45) Date of Patent: Feb. 14, 2017

(54) OXIDIZED LDL AS A BIOMARKER FOR NEUROLOGICAL COMPLICATIONS OF PREGNANCY

(71) Applicant: The University of Vermont and State Agricultural College, Burlington, VT (US)

(72) Inventor: Marilyn J. Cipolla, Colchester, VT (US)

(73) Assignee: The University of Vermont and State Agriculture College, Burlington, VT (US)

( * ) Notice: Subject to any disclaimer, the term of this patent is extended or adjusted under 35 U.S.C. 154(b) by 0 days.

(21) Appl. No.: 14/045,038

(22) Filed: Oct. 3, 2013

(65) Prior Publication Data

US 2014/0093517 A1    Apr. 3, 2014

Related U.S. Application Data

(60) Provisional application No. 61/709,297, filed on Oct. 3, 2012.

(51) Int. Cl.
*G01N 33/92* (2006.01)
*C07K 16/28* (2006.01)
*A61K 39/00* (2006.01)

(52) U.S. Cl.
CPC ............. *G01N 33/92* (2013.01); *C07K 16/28* (2013.01); *A61K 2039/505* (2013.01); *C07K 2317/76* (2013.01); *G01N 2800/368* (2013.01)

(58) Field of Classification Search
None
See application file for complete search history.

(56) References Cited

PUBLICATIONS

Genc et al., Arch Gynecol Obstet. Feb. 2011; 284: 1367-1373.*
Lu and Nightingale, Clin Pharmacokinet. 2000; 38: 305-314.*
Karnard et al., Crit Care Med. 2005; 33: S362-S371.*
Omu et al., Med Princ Pract. 2008; 17: 227-232.*
Broughton-Pipkin et al., Journal of Hypertension, 1998; 16: 221-229.*
Xu et al., Tianjin Yiyao (2010), 38(10), 865-867; article in Chinese; English abstract pasted into action.*
Xu et al., Tianjin Yiyao, 2010; 38(10); 865-867; original article in Chinese translation; 10 pages total.*
Hermida et al., Hypertension. 2001; 38[part 2]: 736-741.*
Douglas & Redman, BMJ, 1994; 309: 1395-1400.*
Amburgey et al., Plasma from preeclamptic women increases blood-brain barrier permeability: role of vascular endothelial growth factor signaling. Hypertension. Nov. 2010;56(5):1003-8. doi: 10.1161/HYPERTENSIONAHA.110.158931. Epub Sep 20, 2010.
Belo et al., Changes in LDL size and HDL concentration in normal and preeclamptic pregnancies. Atherosclerosis. Jun. 2002;162(2):425-32.
Branch et al., Pre-eclampsia and serum antibodies to oxidised low-density lipoprotein. Lancet. Mar. 12, 1994;343(8898):645-6.
Buhimschi et al., The nitric oxide pathway in pre-eclampsia: pathophysiological implications. Hum Reprod Update. Jan.-Feb. 1998;4(1):25-42.
Chen et al., Oxidized low density lipoprotein receptor-1 mediates oxidized low density lipoprotein-induced apoptosis in human umbilical vein endothelial cells: role of reactive oxygen species. Vascul Pharmacol. Jul. 2007;47(1):1-9. Epub Jan. 30, 2007.
Cipolla et al., Inhibition of protein kinase Cβ reverses increased blood-brain barrier permeability during hyperglycemic stroke and prevents edema formation in vivo. Stroke. Nov. 2011;42(11):3252-7. doi:10.1161/STROKEAHA.111.623991. Epub Aug. 18, 2011.
Cipolla, Cerebrovascular function in pregnancy and eclampsia. Hypertension. Jul. 2007;50(1):14-24. Epub Jun. 4, 2007.
Cipolla et al., Pregnancy prevents hypertensive remodeling of cerebral arteries: a potential role in the development of eclampsia. Hypertension. Mar. 2006;47(3):619-26. Epub Dec. 27, 2005.
Cominacini et al., The binding of oxidized low density lipoprotein (ox-LDL) to ox-LDL receptor-1 reduces the intracellular concentration of nitric oxide in endothelial cells through an increased production of superoxide. J Biol Chem. Apr. 27, 2001;276(17):13750-5. Epub Jan. 24, 2001.
Amburgey et al., Plasma from preeclamptic women increases blood-brain barrier permeability: role of vascular endothelial growth factor signaling. Hypertension. Nov. 2010;56(5):1003-8. doi:10.1161/Hypertensionaha.110.158931. Epub Sep. 20, 2010.
Belo et al., Changes in LDL size and HDL conecntration in normal and preeclamptic pregnancies. Atherosclerosis. Jun. 2002;162(2):425-32.
Buhimschi et al., The nitric oxide pathway in pre-eclampsia: pathophysiological implications. Jum Reprod Update. Jan.-Feb. 1998;4(1):25-42.
Cominacini et al., The binding of oxidized low density lipoprotein (ox-LDL) to ox-LDL receptor-1 reduces the intracelluar concentration of nitric oxide in endothelial cells through an increased production of superoxide. J Biol Chem Apr. 27, 2001;276(17):13750-5. Epub Jan. 24, 2011.
Enquobahrie et al., Maternal plasma lipid concentrations in early pregancy and risk of preeclampsia. Am J Hypertens. Jul. 2004;17(7):574-81.
Euser et al., Cerebral blood flow autoregulation and edema formation during pregnancy in anesthetized rats. Hypertension. Feb. 2007;49(2):334-40. Epub Jan. 2, 2007.
Hubel et al., Small low-density lipoproteins and vascular cell adhesion molecule-1 are increased in association with hyperlipidemia in preeclampsia. Metabloism. Oct. 1998;47(10):1281-8.

(Continued)

*Primary Examiner* — Christina Borgeest
(74) *Attorney, Agent, or Firm* — Wolf, Greenfield & Sacks, P.C.

(57) ABSTRACT

Methods for diagnosing and treating conditions associated with life-threatening neurological complications are provided. The methods involve in some aspects the identification of oxLDL and LOX-1 as critical players in pregnant subjects and in some cases subjects having severe preeclampsia (early onset preeclampsia). Related products and kits are also provided.

11 Claims, 5 Drawing Sheets

(56) References Cited

PUBLICATIONS

Kim et al., Paraoxonase gene polymorphism, serum lipid, and oxidized low-density lipoprotein in preeclampsia. Eur J Obstet Gynecol Reprod Biol. Jul. 2007;133(1):47-52. Epub Sep. 1, 2006.

Lee et al., Expression of lectin-like oxidized low-density lipoprotein receptor-1 (LOX-1) in human preeclamptic placenta: possible implications in the process of trophoblast apoptosis. Placenta. Feb.-Mar. 2005;26(2-3):226-33.

Lin et al., Resveratrol protects against oxidized LDL-induced breakage of the blood-brain barrier by lessening disruption of tight junctions and apoptotic insults to mouse cerebrovascular endothelial cells. J Nutr. Dec. 2010;140(12):2187-92. doi: 10.3945/jn.110.123505. Epub Oct. 27, 2010.

Morton et al., Lectin-like oxidized low-density lipoprotein 1 receptor in a reduced uteroplacental perfusion pressure rat model of preeclampsia. Hypertension. May 2012;59(5):1014-20. doi: 10.1161/Hypertensionaha.112.191825. Epub Mar. 5, 2012.

Myatt et al., Vascular biology of preeclampsia. J Thromb Haemost. Mar. 2009;7(3):375-84. doi: 10.1111/j.1538-7836.2008.03259.x.

Nakano et al., LOX-1 mediates vascular lipid retention under hypertensive state. J Hypertens. Jun. 2010;28(6):1273-80. doi: 10.1097/HJH.0b013e32833835d4.

OGGE et al., Placental lesions associated with maternal underperfusion are more frequent in early-onset than in late-onset preeclampsia. J Perinat Med. Nov. 2011;39(6):641-52. doi: 10.1515/JPM.2011.098. Epub Aug. 17, 2011.

Palomares et al., Peroxynitrite decomposition with FeTMPyP improves plasma-induced vascular dysfunction and infarction during mild but not severe hyperglycemic stroke. J Cereb Blood Flow Metab. Jun. 2012;32(6):1035-45. doi: 10.1038/jcbfm.2012.14. Epub Feb. 29, 2012.

Pecks et al., The evaluation of the oxidative state of low-density lipoproteins in intrauterine growth restriction and preeclampsia. Hypertens Pregnancy. 2012;31(1):156-65. doi: 10.3109/10641955.2010.544805. Epub Jan. 20, 2011.

Qiu et al., Oxidized low-density lipoprotein (Oxidized LDL) and the risk of preeclampsia. Physiol Res. 2006;55(5):491-500. Epub Dec. 12, 2005.

Redman et al., Latest advances in understanding preeclampsia. Science. Jun. 10, 2005;308(5728):1592-4.

Reyes et al., Angiogenic imbalance and plasma lipid alterations in women with preeclampsia from a developing country. Growth Factors. Jun. 2012;30(3):158-66. doi: 10.3109/08977194.2012.674035. Epub Apr. 10, 2012.

Roberts et al., PPAR-gamma agonist rosiglitazone reverses increased cerebral venous hydraulic conductivity during hypertension. Am J Physiol Heart Circ Physiol. Oct. 2009;297(4):H1347-53. doi:10.1152/ajpheart.00630.2009. Epub Aug. 7, 2009.

Roggensack et al., Evidence for peroxynitrite formation in the vascularture of women with preeclampsia. Hypertension. Jan. 1999;33(1):83-9.

Sanchez et al., A case-control study of oxidized low density lipoproteins and preeclampsia risk. Gynecol Endocrinol. Oct. 2005;21(4):193-9.

Sankaralingam et al., Increased lectin-like oxidized low-density lipoprotein receptor-1 expression in the maternal vasculature of women with preeclampsia: role for peroxynitrite. Hypertension. Feb. 2009;53(2):270-7. doi: 10.1161/HYPERTENSIONAHA.108.122630. Epub Dec. 22, 2008.

Schreurs et al., The adaptation of the blood-brain barrier to vascular endothelial growth factor and placental growth factor during pregnancy. FASEB J. Jan. 2012;26(1):355-62. doi: 10.1096/fj.11-191916. Epub Sep. 12, 2011.

Schreurs et al., Increased oxidized low-density lipoprotein causes blood-brain barrier disruption in early-onset preeclampsia through LOX-1. FASEB J. Mar. 2013;27(3):1254-63. doi: 10.1096/fj.12-222216. Epub Dec. 10, 2012.

Uzun et al., Circulating oxidized low-density lipoprotein and paraoxonase activity in preeclampsia. Gynecol Obstet Invest. 2005;60(4):195-200. Epub Jul. 26, 2005.

Von Dadelszen et al., Subclassification of preeclampsia.Hypertens Pregnancy. 2003;22(2):143-8.

Wikström et al., Evidence of increased oxidative stress and a change in the plasminogen activator inhibitor (PAI)-1 to PAI-2 ratio in early-onset but not late-onset preeclampsia. Am J Obstet Gynecol. Dec. 2009;201(6):597.e1-8. doi: 10.1016/j.ajog.2009.06.024. Epub Aug. 15, 2009.

Zeeman, Neurologic complications of pre-eclampsia. Semin Perinatol. Jun. 2009;33(3):166-72. doi: 10.1053/j.semperi.2009.02.003.

Euser et al., Magnesium sulfate for the treatment of eclampsia: a brief review. Stroke. Apr. 2009;40(4):1169-75. doi: 10.1161/STROKEAHA.108.527788. Epub Feb. 10, 2009.

Johnson et al., Magnesium sulfate treatment reverses seizure susceptibility and decreases neuroinflammation in a rat model of severe preeclampsia. PLoS One. Nov. 19, 2014;9(11):e113670. doi: 10.1371/journal.pone.0113670. eCollection 2014.

\* cited by examiner

OXIDIZED LDL AS A BIOMARKER FOR NEUROLOGICAL COMPLICATIONS OF PREGNANCY

RELATED APPLICATIONS

This application claims priority under 35 U.S.C. §119(e) to U.S. Provisional Application Ser. No. 61/709,297, entitled "OXIDIZED LDL AS A BIOMARKER FOR NEUROLOGICAL COMPLICATIONS OF PREGNANCY," filed on Oct. 3, 2012, which is herein incorporated by reference in its entirety.

FEDERALLY SPONSORED RESEARCH

This invention was made with government support under Grant No. NS045940 and NS045940-06S1 awarded by NINDS. The government has certain rights in this invention.

FIELD OF THE INVENTION

Aspects of the invention relate to diagnosing and predicting neurological complications of pregnancy and/or preeclampsia as well as related products and kits. Methods of treating preeclampsia are also provided.

BACKGROUND

Preeclampsia is a condition that develops during the last half of pregnancy and is associated with significant maternal and fetal morbidity and mortality. Because there is no effective screening test to diagnose or assess the risk of developing preeclampsia and associated hypertensive disorders, pregnant women cannot receive effective monitoring or treatment until long after complications associated with the disorders, including increased blood pressure and proteinuria, have developed. In addition, pregnant women with little to no risk of developing preeclampsia or associated hypertensive disorders must undergo unnecessary testing for symptoms throughout their pregnancy because there is no effective means by which caregivers may exclude them from risk in the early stages of pregnancy. Additionally, patients having milder forms of preeclampsia are not distinguished from those patients having severe preeclampsia and thus may receive unnecessary treatments.

SUMMARY OF INVENTION

In some aspects the invention is a method for identifying a subject at risk of neurological complications associated with pregnancy by isolating a tissue sample from a pregnant subject, determining a level of oxLDL in the pregnant subject, determining the subject is at risk of neurological complications associated with pregnancy if the oxLDL levels are greater than a control level. The oxLDL levels in some embodiments are greater than 1,600 ng/ml.

The tissue sample is a blood sample in some embodiments.

In some embodiments the method also involves providing a course of treatment for the subject if the subject is identified as at risk of neurological complications associated with pregnancy. Optionally the subject may be administered an anti-seizure prophylaxis, such as magnesium sulfate.

The levels of oxLDL may be measured using any known methods in the art. For instance, the levels of oxLDL may be measured using an antibody assay and/or using a kit for detecting oxLDL.

The subject, in some embodiments is in the first, second or third trimester of pregnancy.

The method may also involve measuring the blood pressure and/or cholesterol of the subject. In some instances the blood pressure of the subject is within normal levels and/or the cholesterol of the subject is above normal levels.

A method for treating a subject is also provided according to aspects of the invention. The method involves administering to a pregnant subject, optionally having preeclampsia, wherein the pregnancy is associated with neurological complications, an oxLDL inhibitor or LOX-1 inhibitor in an effective amount to treat the subject. In some embodiments the pregnant subject is identified as a subject having elevated levels of oxLDL.

In some embodiments the subject does not have an inflammatory disorder and/or the subject has not been diagnosed with an inflammatory disorder.

The subject is administered an oxLDL inhibitor in some embodiments. The oxLDL inhibitor may be an anti-oxLDL binding peptide such as an anti-oxLDL antibody, for instance.

In other embodiments the subject is administered a LOX-1 inhibitor. The LOX-1 inhibitor may be, for example, an anti-LOX-1 binding peptide, such as an anti-LOX-1 antibody or an inhibitory nucleic acid.

The invention in other aspects is a method for treating a subject by administering to a pregnant subject having a condition associated with neurological complications an antioxidant in an effective amount to treat the subject. In some embodiments the subject has been diagnosed with preeclampsia associated with neurological complications according to the methods described herein. In other embodiments the antioxidant is a superoxide dismutase mimetic, Tempol, $ONOO^-$ scavengers such as FeTMPyP (Fe(III) tetrakis(1-methyl-4-pyridyl)porphyrin pentachlorideporphyrin pentachloride) and FeTPPS (5,10,15,20-Tetrakis(4-sulfonatophenyl)porphyrinato Iron (III), Chloride), a compound that reduces reactive nitrogen species, a compound that reduces reactive oxygen species, and ebselen.

In other aspects of the invention, a kit is provided. The kit includes one or more containers housing a reagent for detecting oxLDL levels and instructions for diagnosing pregnancy associated with neurological complications. In some embodiments the reagent for detecting oxLDL is an oxLDL antibody. In other embodiments the reagent for detecting oxLDL is an oxLDL nucleic acid. In yet other embodiments the instructions for diagnosing pregnancy associated with neurological complications refer to determining a level of oxLDL in a pregnant subject wherein the subject is at risk of neurological complications associated with pregnancy if the oxLDL levels are greater than a control level.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF DRAWINGS

FIG. 3A shows a graph of OxLDL levels in plasma from women with EPE compared to LPE, NP and NonP women. Plasma from EPE women had a 260% increase in oxLDL compared to plasma from LPE women.

FIG. 4A is a graph showing hydraulic conductivity ($L_P$) at 36 minutes as a measure of BBB permeability in cerebral veins of NonP rats in response to plasma from LPE and plasma from EPE women with and without the addition of 50 µM FeTMPyP. FeTMPyP inhibited the BBB permeability induced by plasma from EPE women. FIG. 4B is a graph showing $L_p$ as a measure of BBB permeability in response to untreated of plasma from NonP and EPE women, and in response to plasma from NonP women plus 3.5 µg/ml oxLDL and 50 µM FeTMPyP. FeTMPyP inhibited the BBB permeability induced by 3.5 µg/ml exogenous oxLDL in plasma from NonP women. (**$P<0.01$ vs. all; LPE=late-onset preeclampsia; EPE=early-onset preeclampsia).

FIG. 5A shows hydraulic conductivity ($L_p$) as a measure of BBB permeability at 36 minutes in cerebral veins from late-pregnant control (LP-CTL) rats in response to LP-CTL plasma and from late-pregnant high cholesterol treated (LP-HC) rats in response to LP-HC plasma with and without the addition of 10 µg/ml LOX-1 antibody. LP-HC rats showed a significant increase in BBB permeability that could be inhibited with the addition of LOX-1 antibody. FIG. 5B shows mRNA expression of LOX-1 in cerebral veins from LP-CTL and LP-HC animals. There was no difference in mRNA expression of LOX-1 in cerebral veins from LP-HC vs. LP-CL animals. (*$P<0.05$ vs. all; LP-CTL=late pregnant control; LP-HC=late pregnant high cholesterol treated).

DETAILED DESCRIPTION OF INVENTION

Figure 1:
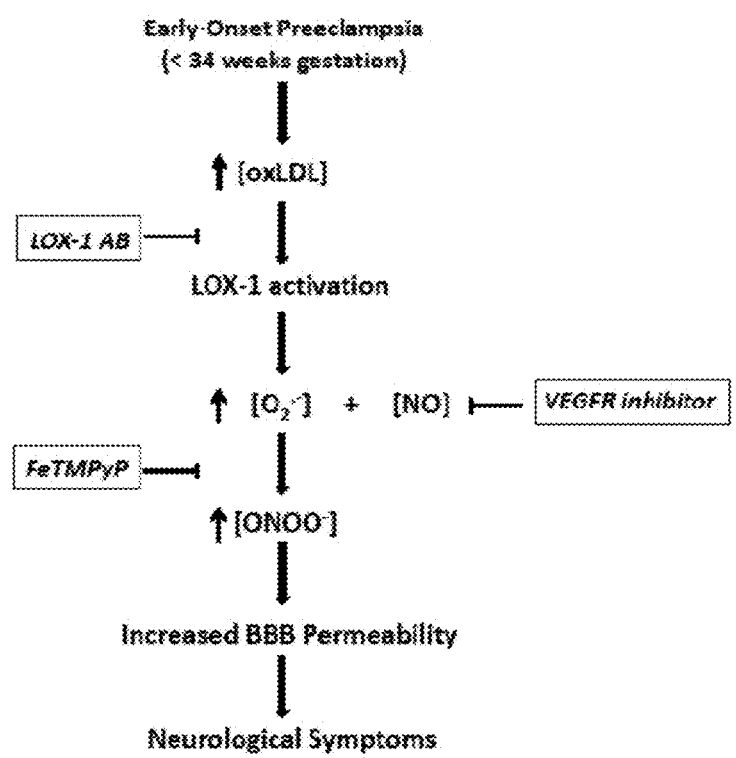
FIG. 1 is a flowchart showing the proposed mechanism leading to neurological complications in early-onset preeclampsia. Increased levels of oxLDL in plasma from EPE women bind to its receptor LOX-1 and induce production of superoxide ($O_2^-$) that will generate peroxynitrite ($ONOO^-$). Increased generation of $ONOO^-$ causes disruption of BBB and increased BBB permeability that is responsible for neurological complications in preeclampsia.

Vasogenic brain edema is a major contributor to the occurrence of neurological symptoms in preeclampsia and is the result of increased cerebrovascular permeability and disruption of the blood-brain bather (BBB). The cerebral endothelium that comprises the BBB contains complex high electrical resistance tight junctions that prevent traffic of ions and large proteins into the brain, resulting in low hydraulic conductivity ($L_p$). BBB disruption causes vasogenic edema and the passage of damaging proteins and plasma constituents into the brain parenchyma. The inventor has previously established that circulating factors in plasma from preeclamptic, but not normal pregnant women, increased BBB permeability, suggesting involvement of circulating factors in BBB disruption in preeclampsia. In that study, plasma from preeclamptic women with severe disease (defined with American College of Obstetricians and Gynecologists criteria) was used, but early-onset preeclampsia (EPE) and late-onset preeclampsia (LPE) were not distinguished. The invention is based at least in part on the discovery that the plasma from EPE women has a greater impact on BBB disruption that underlies neurological symptoms and further involves the discovery of a key factor involved in that process. The increased BBB permeability in response to the plasma from the preeclamptic women was prevented by the inhibition of vascular endothelial growth factor (VEGF) signaling. However, VEGF levels were not increased in plasma from preeclamptic women, suggesting other circulating factors are responsible for increasing BBB permeability. Understanding what circulating factors in plasma from preeclamptic women increase BBB permeability and its underlying mechanism may provide a therapeutic target to prevent and/or predict neurological complications during preeclampsia.

It has been shown that increased oxidized LDL (oxLDL) levels and expression of LOX-1 (oxLDL receptor) in the systemic vasculature in women with preeclampsia. Here we discovered that oxLDL binding to LOX-1 plays a critical role in BBB disruption that underlies the pathogenesis of neurological complications of preeclampsia. Specifically it has been shown according to the invention that increased oxLDL in EPE, through activation of LOX-1, is an underlying mechanism by which BBB disruption occurs in EPE women. The plasma from EPE women significantly increased BBB permeability compared to LPE women through increased levels of oxLDL, activation of LOX-1 and subsequent $ONOO^-$ generation. Additionally, an animal model of high-cholesterol in pregnancy was developed to show that elevated LDL adversely affects pregnancy outcome and causes BBB disruption as seen in EPE.

It was also demonstrated, according to the invention, as shown in the Examples, that circulating factors in plasma from EPE women significantly increased BBB permeability compared to plasma from LPE women that was prevented by inhibiting LOX-1. Circulating oxLDL, the major ligand of LOX-1, was significantly increased in plasma from EPE women (by 260%) compared to LPE women. Exogenous oxLDL added to plasma from non-pregnant women also increased BBB permeability comparable to EPE. Additionally, the selective $ONOO^-$ decomposition catalyst FeTMPyP inhibited increased BBB permeability induced by plasma from EPE women or induced by exogenous oxLDL. Finally, a rat model of pathologically high lipid levels in pregnancy showed a significant increase in blood pressure and adverse effects on pregnancy outcome, similar to EPE. BBB permeability was also increased in response to high levels of cholesterol that could be prevented by blocking LOX-1. Taken together, these results show for the first time that plasma from EPE women significantly increase BBB permeability compared to LPE women through increased oxLDL levels that activate LOX-1, resulting in increased $ONOO^-$ generation.

Therefore, the invention involves, in some aspects, a method for identifying a subject at risk of neurological complications associated with pregnancy. The method is performed by isolating a tissue sample from a pregnant subject, determining a level of oxLDL in the pregnant subject, and determining that the subject is at risk of neurological complications associated with pregnancy if the oxLDL levels are greater than a control level.

A "subject at risk of neurological complications associated with pregnancy", as used herein, is a subject that is pregnant that could develop neurological complications or in some instances a subject that has recently pregnant and experienced neurological complications such as seizure but is no longer pregnant. In some instances the pregnant subject has been diagnosed with preeclampsia.

As used herein, "preeclampsia" is a disorder that occurs during, which affects both the mother and the unborn baby and is associated with hypertension and proteinuria after the $20^{th}$ week of pregnancy. Patients having preeclampsia can be classified as EPE and LPE. Clinically preeclampsia is defined according to well-established criteria, such as a blood pressure of at least 140/90 mm Hg and urinary excretion of at least 0.3 grams of protein in a 24-hour urinary protein excretion (or at least +1 or greater on dipstick testing), each on two occasions 4-6 hours apart. EPE is also sometimes referred to as, "severe preeclampsia" and can be defined clinically, as a blood pressure of at least 160/110 mm Hg on at least 2 occasions 6 hours apart and greater than 5 grams of protein in a 24-hour urinary protein excretion or persistent +3 proteinuria on dipstick testing. Severe preeclampsia may include HELLP syndrome (hemolysis, elevated liver enzymes, low platelet count). Other elements of EPE may include in-utero growth restriction (IUGR) in less than the 10% percentile according to the US demographics, persistent neurologic symptoms (headache, visual disturbances), epigastric pain, oliguria (less than 500 mL/24 h), serum creatinine greater than 1.0 mg/dL, elevated liver enzymes (greater than two times normal), thrombocytopenia (<100,000 cells/µL) and neurological complications.

Neurological complications associated with pregnancy include but are not limited to seizures, coma, focal motor deficits, cortical blindness, and cerebrovascular hemorrhage. Neurological symptoms are the most serious and life-threatening complications of preeclampsia (1). The appearance of neurological complications accounts for at least 75% of maternal mortality worldwide (2, 3). However, neurological complications do not occur in all women diagnosed with preeclampsia, suggesting differences in the pathogenesis of this disease. Epidemiologic studies have shown that neurological complications occur most often in early-onset preeclampsia (EPE) where hypertension and proteinuria occur before 34 weeks of gestation, compared to late-onset preeclampsia (LPE) that develops after 34 weeks of gestation (4-7). These findings importantly suggest that EPE is a form of preeclampsia that affects the brain more severely, contributing to neurological complications.

The methods involve isolation of a tissue sample from a pregnant subject. A pregnant subject, as used herein is a female mammalian subject that has been identified as being pregnant or who is at risk of being pregnant. A subject is at risk of being pregnant if the subject is capable of having a child and who has been exposed to sperm. In preferred embodiments the pregnant subject is a human subject. A control subject is a normal subject who has been determined not to be pregnant, either by inability to become pregnant or lack of exposure to sperm during critical time points. The isolated tissue sample is a tissue in which oxLDL is expressed. An exemplary tissue sample is blood or a portion thereof, such as plasma.

The pregnant subject may be in any stage of the pregnancy. For instance, the subject may be in the first, second or third trimester of pregnancy.

The subject may be diagnosed as having preeclampsia or such diagnosis may be revealed through the testing methods of the invention. Diagnosis can be achieved using known methods in the art. For instance, the blood pressure of the subject may be measured and may be elevated. However, elevated blood pressure is not essential for a subject to have preeclampsia. Therefore the blood pressure of the subject may be within normal levels. The subject may also be subjected to a test measuring cholesterol levels. In some embodiments the cholesterol levels of the subject are above normal levels.

A level of oxLDL in the pregnant subject is determined in order to assess the status of the preeclampsia. The levels of oxLDL serve as a marker indicating the presence or absence of neurological complications associated with preeclampsia. The term "marker" refers to an organic biomolecule, preferably, a lipid that is differentially present in a sample taken from a subject having EPE as compared to a comparable sample taken from a subject who has LPE or from a normal subject, who does not have preeclampsia and/or is not pregnant. A marker is differentially present in samples from subjects having EPE, if it is present at an elevated level in the subject with EPE, as compared to a control level. A control level may be a level of oxLDL found in samples from normal subjects and/or subjects having LPE or alternatively a standard control level. A subject having elevated levels of oxLDL is one who is at risk of neurological complications associated with pregnancy.

OxLDL has a greater negative charge compared to native LDL and thus oxLDL, but not native LDL, is available to bind the lectin-like oxidized LDL receptor 1 (LOX-1) that is predominantly expressed on endothelial cells. Under normal physiological conditions LOX-1 activity is low, but its increased activation during disease states such as atherosclerosis, diabetes and hypertension causes endothelial dysfunction. LOX-1 activation rapidly stimulates the production of superoxide in endothelial cells, mainly through activation of NADPH oxidase. Superoxide decreases the concentration of nitric oxide (NO) by binding NO to form peroxynitrite ($ONOO^-$), a relatively stable reactive oxygen and nitrogen species that has deleterious effects on cell viability and endothelial function. $ONOO^-$ generation has been reported in the systemic vasculature in women with preeclampsia, however, whether $ONOO^-$ generation, secondary to LOX-1 activation, is also involved in disrupting the BBB during preeclampsia is not known. It has been demonstrated according to the invention that $ONOO^-$ generation, secondary to LOX-1 activation, causes increased BBB permeability in women with EPE.

Once a subject is diagnosed as having increased oxLDL levels during pregnancy a therapeutic course of treatment can be applied. The subject being treated is a subject having pregnancy associated with neurological complications. The subject may be identified as a subject having elevated levels of oxLDL. Alternatively, the subjects having pregnancy associated with neurological complications treated according to the methods of the invention may be identified by other methods known in the art. For instance the subject may be a pregnant subject who has experienced seizures. In some embodiments the subject does not have an inflammatory disorder. In other embodiments the subject has not been diagnosed with an inflammatory disorder.

The therapeutic treatment applied to the subject may be a traditional therapeutic for treating the symptoms of preeclampsia. For instance, the subject may be treated with an anti-seizure prophylaxis or therapeutic. The anti-seizure prophylaxis may be, for instance, magnesium sulfate.

Alternatively, the therapeutic method may be a therapeutic method of the invention. For instance, the therapeutic method may involve administration of an oxLDL inhibitor, an LOX-1 inhibitor, or an antioxidant.

An oxLDL inhibitor, as used herein, refers to a compound that can reduce oxLDL activity and/or levels in a subject. These inhibitors include but are not limited to small molecule inhibitors, nucleic acid inhibitors and peptide based inhibitors. Small molecule inhibitors include but are not limited to atorvastatin, as well as analogs and variants thereof. A LOX-1 inhibitor, as used herein, refers to a compound that can reduce LOX-1 activity and/or levels in a subject. These inhibitors include but are not limited to small molecule inhibitors, nucleic acid inhibitors and peptide based inhibitors. Small molecule inhibitors include but are not limited to statins and procyanidins, as well as analogs and variants thereof.

The oxLDL inhibitor and LOX-1 inhibitor may also be binding peptides. An anti-oxLDL binding peptide is a peptide that binds specifically to oxLDL and interferes with its activity. The binding peptide may be an anti-oxLDL antibody. An anti-LOX-1 binding peptide is a peptide that binds specifically to LOX-1 and interferes with its activity. The binding peptide may be an anti-LOX-1 antibody. Antibodies, including fragments thereof, single chain antibodies etc. are well known in the art.

The subject may also be administered an antioxidant in an effective amount to treat the subject. An antioxidant is a compound that inhibits the oxidation of other molecules. Antioxidants include but are not limited to superoxide dismutase mimetics, Tempol, $ONOO^-$ scavengers such as FeTMPyP and FeTPPS, and ebselen.

When used in combination with the therapies of the invention the dosages of known therapies may be reduced in some instances, to avoid side effects.

The active agents of the invention are administered to the subject in an effective amount for treating the subject. An "effective amount", for instance, is an amount necessary or sufficient to realize a desired biologic effect. For instance an effective amount is that amount sufficient to prevent or inhibit neurological complications of preeclampsia.

The effective amount of a compound of the invention in the treatment of a subject may vary depending upon the specific compound used, the mode of delivery of the compound, and whether it is used alone or in combination. The effective amount for any particular application can also vary depending on such factors as the type and/or degree of infection in a subject, the particular compound being administered for treatment, the size of the subject, or the severity of the disorder. One of ordinary skill in the art can empirically determine the effective amount of a particular molecule of the invention without necessitating undue experimentation. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity in and of itself and yet is entirely effective to treat the particular subject.

Toxicity and efficacy of the protocols of the present invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays, animal studies and human studies can be used in formulating a range of dosage of the prophylactic and/or therapeutic agents for use in humans. The dosage of such agents lies preferably within a range of circulating concentrations that include the ED50 with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

As used herein, the term treat, treated, or treating when used with respect to a disorder refers to a prophylactic treatment which increases the resistance of a subject to development of the disease or, in other words, decreases the likelihood that the subject will develop the disease as well as a treatment after the subject has developed the disease in order to fight the disease, prevent the disease from becoming worse, or slow the progression of the disease compared to in the absence of the therapy. A prophylactic is desired for instance if a pregnant subject has had prior instances of EPE in prior pregnancies.

Multiple doses of the molecules of the invention are also contemplated. In some instances, when the molecules of the invention are administered with another therapeutic, for instance, a chemotherapeutic agent a sub-therapeutic dosage of either or both of the molecules may be used. A "sub-therapeutic dose" as used herein refers to a dosage which is less than that dosage which would produce a therapeutic result in the subject if administered in the absence of the other agent.

Pharmaceutical compositions of the present invention comprise an effective amount of one or more agents, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. Moreover, for animal (e.g., human) administration, it will be understood that preparations should meet sterility, pyrogenicity, general safety and purity standards as required by FDA Office of Biological Standards. The compounds are generally suitable for administration to humans. This term requires that a compound or composition be nontoxic and sufficiently pure so that no further manipulation of the compound or composition is needed prior to administration to humans.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences (1990), incorporated herein by reference). Except insofar as any conventional carrier is incompatible with the active ingredient, its use in the therapeutic or pharmaceutical compositions is contemplated. The compounds may be sterile or non-sterile.

The agent may comprise different types of carriers depending on whether it is to be administered in solid, liquid or aerosol form, and whether it need to be sterile for such routes of administration as injection. The present invention can be administered intravenously, intradermally, intraarterially, intralesionally, intratumorally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences (1990), incorporated herein by reference).

In any case, the composition of oxLDL or LOX-1 inhibitor may further comprise various antioxidants to retard oxidation of one or more components as well as to treat the disease. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The agent may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups also can be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

The compounds of the invention may be administered directly to a tissue. Direct tissue administration may be achieved by direct injection. The compounds may be administered once, or alternatively they may be administered in a plurality of administrations. If administered multiple times, the compounds may be administered via different routes. For example, the first (or the first few) administrations may be made directly into the affected tissue while later administrations may be systemic.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients. In general, a pharmaceutical composition comprises the compound of the invention and a pharmaceutically-acceptable carrier. Pharmaceutically-acceptable carriers for nucleic acids, small molecules, peptides, monoclonal antibodies, and antibody fragments are well-known to those of ordinary skill in the art. As used herein, a pharmaceutically-acceptable carrier means a non-toxic material that does not interfere with the effectiveness of the biological activity of the active ingredients.

Pharmaceutically acceptable carriers include diluents, fillers, salts, buffers, stabilizers, solubilizers and other materials which are well-known in the art. Exemplary pharmaceutically acceptable carriers for peptides in particular are described in U.S. Pat. No. 5,211,657. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The compounds of the invention may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

Compositions suitable for oral administration may be presented as discrete units, such as capsules, tablets, lozenges, each containing a predetermined amount of the active agent. Other compositions include suspensions in aqueous liquids or non-aqueous liquids, such as a syrup, an elixir or an emulsion.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. Techniques for preparing aerosol delivery systems are well known to those of skill in the art. Generally, such systems should utilize components which will not significantly impair the biological properties of the active agent (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing aerosols without resort to undue experimentation.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

Both non-biodegradable and biodegradable polymeric matrices can be used to deliver the agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

The invention also encompasses various assays for diagnostic and therapeutic purposes as discussed above and related kits to achieve the methods. The diagnostic methods may achieve for instance using protein or lipoprotein detection assays for detecting and measuring expression levels of oxLDL.

Detection of a protein or lipoprotein in a test sample involves routine methods. The skilled artisan can detect the presence or absence of a protein using well known methods. One such method is an immunoassay. In general, immunoassays involve the binding of proteins in a sample to a solid phase support such as a plastic surface. Detectable antibodies are then added which selectively bind to the protein of interest. Detection of the antibody indicates the presence of the protein. The detectable antibody may be a labeled or an unlabeled antibody. Unlabeled antibody may be detected using a second, labeled antibody that specifically binds to the first antibody or a second, unlabeled antibody which can be detected using labeled protein A, a protein that complexes with antibodies. Various immunoassay procedures are described in Immunoassays for the 80's, A. Voller et al., Eds., University Park, 1981, and The Immunoassay Handbook, Third Edition, David Geoffrey Wild (Ed), 2005 which are incorporated herein by reference.

Simple immunoassays such as a dot blot and a Western blot involve the use of a solid phase support which is contacted with a test sample. Any proteins present in the test sample bind the solid phase support and can be detected by a specific, detectable antibody preparation. The intensity of the signal can be measured to obtain a quantitative readout. Other more complex immunoassays include forward assays for the detection of a protein in which a first anti-protein antibody bound to a solid phase support is contacted with the test sample. After a suitable incubation period, the solid phase support is washed to remove unbound protein. A second, distinct anti-protein antibody is then added which is specific for a portion of the specific protein not recognized by the first antibody. The second antibody is preferably detectable. After a second incubation period to permit the detectable antibody to complex with the specific protein bound to the solid phase support through the first antibody, the solid phase support is washed a second time to remove the unbound detectable antibody. Alternatively, in a forward sandwich assay a third detectable antibody, which binds the second antibody is added to the system. Other types of immunometric assays include simultaneous and reverse assays. A simultaneous assay involves a single incubation step wherein the first antibody bound to the solid phase support, the second, detectable antibody and the test sample are added at the same time. After the incubation is completed, the solid phase support is washed to remove unbound proteins. The presence of detectable antibody associated with the solid support is then determined as it would be in a conventional assays. A reverse assay involves the stepwise addition of a solution of detectable antibody to the test sample followed by an incubation period and the addition of antibody bound to a solid phase support after an additional incubation period. The solid phase support is washed in conventional fashion to remove unbound protein/antibody complexes and unreacted detectable antibody.

A number of methods are well known for the detection of antibodies. For instance, antibodies can be detectably labeled by linking the antibodies to an enzyme and subsequently using the antibodies in an enzyme immunoassay (EIA) or enzyme-linked immunosorbent assay (ELISA), such as a capture ELISA. The enzyme, when subsequently exposed to its substrate, reacts with the substrate and generates a chemical moiety which can be detected, for example, by spectrophotometric, fluorometric or visual means. Enzymes which can be used to detectably label antibodies include, but are not limited to malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

A detectable label is a moiety, the presence of which can be ascertained directly or indirectly. Generally, detection of the label involves an emission of energy by the label. The label can be detected directly by its ability to emit and/or absorb photons or other atomic particles of a particular wavelength (e.g., radioactivity, luminescence, optical or electron density, etc.). A label can be detected indirectly by its ability to bind, recruit and, in some cases, cleave another moiety which itself may emit or absorb light of a particular wavelength (e.g., epitope tag such as the FLAG epitope, enzyme tag such as horseradish peroxidase, etc.). An example of indirect detection is the use of a first enzyme label which cleaves a substrate into visible products. The label may be of a chemical, peptide or nucleic acid molecule nature although it is not so limited. Other detectable labels include radioactive isotopes such as P32 or H3, luminescent markers such as fluorochromes, optical or electron density markers, etc., or epitope tags such as the FLAG epitope or the HA epitope, biotin, avidin, and enzyme tags such as horseradish peroxidase, *-galactosidase, etc. The label may be bound to a peptide during or following its synthesis. There are many different labels and methods of labeling known to those of ordinary skill in the art. Examples of the types of labels that can be used in the present invention include enzymes, radioisotopes, fluorescent compounds, colloidal metals, chemiluminescent compounds, and bioluminescent compounds. The coupling or conjugation of these labels to the antibodies can be performed using standard techniques common to those of ordinary skill in the art.

Another labeling technique which may result in greater sensitivity consists of coupling the molecules described herein to low molecular weight haptens. These haptens can then be specifically altered by means of a second reaction. For example, it is common to use haptens such as biotin, which reacts with avidin, or dinitrophenol, pyridoxal, or fluorescein, which can react with specific anti-hapten antibodies.

In one embodiment, a kit comprises an inhibitor of oxLDL and/or LOX-1 and instructions for administering the same. The kit may further comprise devices for administering the inhibitors, and/or other therapeutics or diagnostics related to the therapy. The kit may also include antioxidants or other useful therapeutics as well as articles to enable delivery of the compounds to the subject.

In other embodiments the kit may include a reagent for detecting oxLDL levels and instructions for diagnosing pregnancy associated with neurological complications. Reagents for detecting oxLDL include binding peptides such as oxLDL antibodies or oxLDL nucleic acid.

The instructions for diagnosing pregnancy associated with neurological complications may refer to determining a level of oxLDL in a pregnant subject. "Instructions" can define a component of promotion, and typically involve written instructions on or associated with packaging of compositions of the invention. Instructions also can include any oral or electronic instructions provided in any manner.

Thus the agents described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include one or more agents described herein, along with instructions describing the intended therapeutic application and the proper administration of these agents. In certain embodiments agents in a kit may be in a pharmaceutical formulation and dosage suitable for a particular application and for a method of administration of the agents.

The kit may be designed to facilitate use of the methods described herein by physicians and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for human administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N+(C1-4alkyl)4 salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As used herein, the term "prodrug" means a biologically active derivative of a compound that can hydrolyze, oxidize, or otherwise react under biological conditions (in vitro or in vivo) to provide the pharmacologically active compound. In this instance, the "prodrug" is a compound administered to a subject, and the pharmacologically active compound is the "active metabolite thereof." In certain cases, a prodrug has improved physical and/or delivery properties over the parent compound. Prodrugs are typically designed to enhance pharmaceutically and/or pharmacokinetically based properties associated with the parent compound. The advantage of a prodrug can lie in its physical properties, such as enhanced water solubility for parenteral administration at physiological pH compared to the parent compound, or it enhances absorption from the digestive tract, or it may enhance drug stability for long-term storage.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Summary:

The following examples demonstrate for the first time that high levels of oxLDL in EPE increase BBB permeability through LOX-1 activation and subsequent ONOO$^-$ generation. Also, a rat model of high cholesterol in pregnancy confirmed the damaging effects of high levels of LDL that was comparable to EPE. This is the first report that identifies that only circulating factors in EPE increase BBB permeability compared to LPE. In addition, the data establishes a mechanism for BBB disruption in EPE that might be helpful in improving the identification and treatment of neurological complications in pregnant women. Further studies are required to determine how this BBB disruption induced by oxLDL leads to actual neurological symptoms, which could lead to treatment or prevention of these complications in preeclampsia.

The cerebral endothelium that comprises the BBB provides a strong protective mechanism against vasogenic brain edema (11). As we have shown previously, circulating factors released in preeclampsia can disrupt the BBB that may lead to vasogenic edema, the greatest contributor of neurological complications in preeclampsia (13). Here, the inventors have demonstrated for the first time that intraluminal exposure of plasma from EPE women in the cerebral vein of Galen for 3 hours significantly increased BBB permeability compared to plasma from LPE or NP women. These new findings are of great clinical importance as they demonstrate that EPE women are at significant risk for neurological complications and thereby confirm the epidemiologic studies. Prior studies have not differentiated effects of LPE vs. EPE on BBB permeability. Neal et al. found increased permeability in systemic mesenteric arteries from frogs in response to plasma from severe compared to mild preeclamptic women, however, the severity of preeclampsia was strongly reflected in time of onset (32). We show that EPE and LPE have different etiologies, arising from greater placental underperfusion and subsequent release of circulating factors in EPE compared to LPE and that EPE and LPE should be considered as two entities displaying at least partially different etiologies with EPE having the greatest risk for neurological complications.

We found that oxLDL levels were increased in plasma from EPE women but not in plasma from LPE women that was comparable to NP women. This increase in EPE only compared to LPE and NP may be related to the fact that oxidative stress was found only in placentas from EPE women, suggesting greater capacity for oxidative modification of LDL in EPE. Since oxLDL was increased in plasma from EPE women only, this important finding provides an important biomarker for neurological complications in preeclamptic women.

OxLDL mainly acts through its receptor LOX-1, which has been studied extensively in pathological states such as atherosclerosis, coronary arterial heart disease and hypertension (19, 20). However, data regarding LOX-1 activation in preeclampsia are scarce. LOX-1 was associated with preeclampsia for the first time in a study in 2005 that showed upregulation of LOX-1 in preeclamptic hypoxic placentas (42). Recently, it was found that upregulation of LOX-1 in HUVECs occurred in response to plasma from preeclamptic women and in a rat model of preeclampsia (22, 23). Here, we show for the first time involvement of LOX-1 in increasing BBB permeability in plasma from EPE women. Also, we showed that exogenous oxLDL to the levels as measured in plasma from EPE women significantly increased BBB permeability in cerebral veins, comparable to EPE women. Thus, increased oxLDL may not be just a biomarker for neurological symptoms in EPE, but also the underlying cause. We propose a novel mechanism in that high levels of circulating oxLDL increase BBB permeability in EPE through LOX-1 activation. To our knowledge, only few studies investigated oxLDL and vascular permeability. One study using mouse cultured cerebral endothelial cells showed that oxLDL is able to increase cerebral permeability (30). In the systemic vasculature, Nakano et al. showed increased vascular permeability in mesenteric arteries in spontaneous hypertensive rats pretreated with oxLDL that was also inhibited by a LOX-1 antibody (43). Further, for this study, we did not determine possible upregulation of LOX-1 after exposure to plasma from EPE women because cerebral veins were only incubated for 3 hours. Sankaralingam et al. found LOX-1 upregulation in HUVECs in response to plasma from preeclamptic women after 24 hrs, while after 6 hrs oxidative stress was already increased without upregulation of LOX-1, confirming that increased ligands such as oxLDL activating LOX-1 already have damaging effects on the endothelium. It remains to be determined in cultured cerebral endothelial cells if longer incubation would cause upregulation of LOX-1 expression in response to plasma from EPE women as seen in HUVECs in response to preeclamptic plasma (23).

LOX-1 activation has been shown to induce several intracellular signaling pathways, such as increased expression of chemokines and adhesion molecule, triggering of the CD40/CD40L pathway that activates the inflammatory cascade and increased production of reactive oxygen species in endothelial cells (44). Here, we show that BBB permeability induced by either plasma from EPE women or exogenous oxLDL to the levels of EPE women was inhibited with FeTMPyP, demonstrating that $ONOO^-$ generation caused the increased BBB permeability induced by oxLDL/LOX-1 activation. $ONOO^-$ is generated by the reactive oxygen species superoxide and NO and is known to have deleterious effects on endothelial function (18, 27). Several studies confirm our findings that oxLDL/LOX-1 activation induces ROS and $ONOO^-$ generation. Cominacini et al. showed in bovine artery cultured cells that binding of oxLDL to LOX-1 decreased the intracellular concentration of NO by inducing the production of superoxide through NADPH oxidase (25). Another study using HUVECs found that $ONOO^-$ generation was stimulated by oxLDL (45). One study investigating preeclampsia, showed increased activity of NADPH oxidase and $ONOO^-$ generation in HUVECs after exposure to plasma from preeclamptic women (23). Because NADPH oxidase expression and activity is greater in the cerebral vessels compared to systemic vasculature (46), the brain may be especially vulnerable for activation of NADPH oxidases and subsequent $ONOO^-$ generation. Importantly, $ONOO^-$ also stimulates LOX-1 and a self-perpetuating mechanism develops that could cause extensive endothelial damage with deleterious effects for the maternal cerebral vasculature (18). In addition, these findings would explain the results from our previous study in which the increased BBB permeability was prevented by VEGF receptor inhibition (13). Phosphorylation of VEGF receptors results in release of NO (47), thus, its inhibition would decrease the level of NO available for $ONOO^-$ generation, preventing BBB disruption (FIG. 1).

Finally, we created a rat model with pathologically high levels of LDL in pregnancy to examine pregnancy outcome, blood pressure and BBB permeability with possible LOX-1 involvement as seen in EPE. LP-HC rats showed a modest but significant increase in blood pressure and a lower birth weight, as seen in EPE, compared to LP-CTL animals. Interestingly, these animals also show significantly increased BBB permeability that could be inhibited by blocking LOX-1, suggesting oxidative modification of high levels of LDL in the LP-HC rats comparable as seen in EPE. In contrast to other studies, we did not find upregulation of LOX-1 in this model of preeclampsia. A possible explanation for this difference could be that other studies used HUVECs or large conduct arteries such as the mesenteric artery and aorta, whereas we examined the effect of high cholesterol on cerebral arteries. Regardless, increased BBB permeability in response to increased oxLDL can occur without upregulation of LOX-1 expression, as seen in EPE women.

Materials and Methods:

Patients and human plasma samples. Maternal plasma samples were obtained from an ongoing investigation of preeclampsia (Prenatal Exposures and Preeclampsia Prevention; PEPP) at the Magee-Women's Research Institute and Magee-Womens Hospital, University of Pittsburgh, Pennsylvania. The PEPP study was approved by the University of Pittsburgh institutional review board and informed consent was obtained from all participants. The PEPP committee approves the use of these previously frozen samples and de-identified clinical data. Blood samples from all women were collected into EDTA plasma separation tubes. Plasma was centrifuged at 1400 to 1600 revolutions per minute and aliquoted. Plasma was then pooled from 4 groups: nonpregnant women who had never been pregnant (NonP; n=9), pregnant women with uncomplicated pregnancies (NP; n=12), pregnant women who developed LPE (n=10) and pregnant women who developed EPE (n=5). The pooled plasma was stored at −80° C. until experimentation. The women enrolled in the preeclamptic groups met the criteria according to the American College of Obstetricians and Gynecologists of blood pressure greater than or equal to 140 mmHg systolic and/or 90 mmHg diastolic plus an increase of greater than 30 mmHg systolic and/or 15 mmHg diastolic plus proteinuria greater than 300 mg/24 hrs or at least equal to 2+ protein using a urine dipstick test. EPE women were diagnosed with preeclampsia and delivered before 34 weeks of gestation and LPE women were diagnosed and delivered after 34 weeks of gestation (see Table 1). Only non-smokers and nulliparous women were included during plasma collection for this study.

Measurement of oxLDL in human plasma samples. The levels of oxLDL in the plasma from the NonP, NP, LPE and EPE women were determined using a sandwich Enzyme-Linked-Immuno-Sorbent-Assay (ELISA) Kit (Immunodiagnostik, Bensheim, Germany) according to the manufacturers' instructions. Measurements were performed in triplicate and averaged.

Animals. Female Sprague Dawley virgin nonpregnant rats (12-14 weeks; 250-300 grams) or female Sprague Dawley pregnant rats (day 5; 12-14 weeks, 250-300 grams) were purchased from Charles River (Saint-Constant, QB, Canada). All of the procedures were approved by the University of Vermont Institutional Animal care and Use Committee and complied with the National Institutes of Health Guide for the Care and Use of Laboratory Animals Animals were housed in the Animal Care facility, which is an Association for Assessment and Accreditation of Laboratory Animal Care-accredited facility Animals had access to food and water ad libitum and were maintained on a 12-hour light/dark cycle.

High-cholesterol rat model. The pregnant rats were divided into 2 groups on day 6 of pregnancy: a late-pregnant control group (LP-CTL; n=8) and a late-pregnant high-cholesterol treated group (LP-HC; n=8). The LP-CTL rats received Prolab® 3000 rodent chow for 14 days. The LP-HC animals received a 14 day diet consisting of Prolab® 3000 rodent chow, including 2% cholesterol and 0.5% cholic acid (added to lower hepatic clearance of cholesterol) to increase total and LDL-cholesterol. Experimentation was done on day 14 of the diet that equaled day 20 of pregnancy in all animals.

Blood pressure measurements. All LP-CTL and LP-HC animals had blood pressure measurements taken on day 2 and day 13 of their diet. Animals were trained for 2 days prior to the first day of blood pressure measurements to make the rats familiar with handling and restraint associated with the procedure. This way, we prevented measuring artificially high blood pressures by reducing stress in the animals. Blood pressures were taken using a noninvasive tail cuff method (CODAS 8, Kent Scientific, Torrington, Conn.), as previously done (51). Briefly, animals were placed in individual holders on a heating plate and both an occlusion cuff and a volume pressure-recording cuff were placed on the tail close to the base. Animals were warmed to 30° C. for optimal volume pressure recording. Systolic, diastolic and mean blood pressure, heart pulse rate, tail blood volume, and tail blood flow were measured simultaneously.

Rat plasma samples. Plasma samples were obtained from trunk blood from LP-CTL and LP-HC rats. Plasma was collected in EDTA plasma separation tubes and centrifuged for 10 minutes at 2500 revolutions per minute. Plasma was then aliquoted and directly used for permeability experiments.

BBB permeability measurements. The first set of experiments was performed to determine the effects of circulating factors in plasma from EPE and LPE women on the BBB permeability compared to NP women and NonP women. We measured $L_p$, the critical transport parameter that relates water flux to hydrostatic pressure, in isolated cerebral veins from nonpregnant female rats after perfusing with plasma from the 4 groups of women, as described previously (52). This method of measuring BBB permeability was specifically developed to have a direct measure of water permeability and has been successfully used in several previous studies (13, 52-54).

The vein of Galen was used for all permeability experiments as representation of the BBB because this vein has BBB properties and is where BBB disruption occurs first during acute hypertension (55). Further, only veins from NonP rats were used to isolate the possible effects of circulating factors in the plasma and our previous studies have shown no difference in BBB permeability comparing vessels from NonP and pregnant rats (53). Briefly, cerebral veins were carefully dissected out of the brain of NonP rats and the proximal end mounted on one glass cannula in an arteriograph chamber. Veins were perfused intraluminally with 20% v/v plasma from either NonP (n=7), NP (n=7), LPE (n=6) and EPE (n=6) in a HEPES buffer for 3 hours at 10±0.3 mmHg and 37° C. The distal end of the vessel was tied off with a nylon structure. After this incubation period with plasma, intravascular pressure was increased to 25±0.1 mmHg and the drop in pressure due to transvascular filtration of water out of the vessel in response to hydrostatic pressure was measured for 40 minutes. The decrease of intravascular pressure per minute (mmHg/min) was converted to volume flux across the vessel wall (µm3) using a conversion curve, as previously described (52). After flux was determined, transvascular filtration per surface area (Jv/S) and $L_p$ were calculated by normalizing flux to the surface area and oncotic pressure of the plasma perfusate that was determined by a commercially available oncometer.

In a separate set of experiments, we determined the involvement of LOX-1 activation on BBB permeability by adding a neutralizing antibody to LOX-1 (5 µg/ml; n=6) to the plasma from EPE women before perfusing the plasma into the vein of Galen and the permeability experiment was repeated.

Another set of experiments was performed to determine the involvement of ONOO⁻ generation in plasma from EPE women by adding the ONOO⁻ decomposition catalyst FeTMPyP (50 µM; n=6) to the plasma from EPE women before perfusing the plasma in the cerebral veins. FeTMPyP is a ferric porphyrin complex that catalytically isomerizes peroxynitrite to nitrate in vitro (56). It has been shown to be selective for blocking ONOO⁻ effects without interfering with NO or superoxide (57). Therefore, FeTMPyP serves as a selective ONOO⁻ decomposition catalyst. In addition, the concentration of 50 µM was based on one of our earlier studies where FeTMPyP was used in isolated arteries to scavenge ONOO⁻ (58).

A separate set of experiments was performed to determine the effects of exogenous oxLDL on BBB permeability by the addition of exogenous human oxLDL (3.5 µg/ml; n=7) to plasma from NonP women before perfusing the plasma in the cerebral veins. Thus, we could determine the direct effect of oxLDL on BBB permeability and compare this to the BBB permeability measured in the EPE plasma. For these experiments, plasma from NonP women was chosen rather than plasma from NP women to eliminate other possible circulating factors present in pregnancy that could interact with oxLDL. To determine if there was a causal link between oxLDL increasing BBB permeability and ONOO⁻ generation, we repeated these experiments with the addition of FeTMPyP (50 µM; n=6) to the oxLDL-plasma mixture before perfusion in the vein of Galen and measured $L_p$.

The last set of experiments was performed to determine the involvement of high levels of cholesterol in pregnancy on pregnancy outcome and BBB disruption. The cerebral vein of Galen was carefully dissected out of LP rats that received either a control diet or a high-cholesterol diet and mounted in the arteriograph chamber, as described above. For these experiments, 20% v/v plasma in HEPES buffer was taken and perfused in veins from the same animals. To determine the contribution of oxLDL in increasing BBB permeability in the high-cholesterol treated pregnant rats, the same neutralizing LOX-1 antibody (5 µg/ml; n=8) was added to the plasma from the LP-HC animals before perfusion in the cerebral veins.

Measurement of mRNA expression of LOX-1 using real-time quantitive PCR. The middle cerebral artery (MCA) was used as a representative cerebral vessel to measure mRNA expression of LOX-1 in the LP-CTL and LP-HC animals, as the Vein of Galen was used of for permeability experiments in these animals. Total RNA was extracted from MCAs from LP-CTL (n=6) and LP-HC (n=7) rats using Trizol reagent (Life Technologies) followed by purification using an Rneasy Micro Kit (Qiagen) per manufacture's protocols. RNA concentrations and quality were determined using an Agilent Bioanalyzer (Agilent). Real time PCR was performed in a two-step process. RNA was reverse transcribed using a mix of oligo dT primers and random primers using the iScript cDNA Synthesis Kit (Biorad). For each sample, cDNA was used to amplify the target gene LOX-1 and two generally used housekeeping genes, Hprt1 and Ywhaz. Primers were designed by the Obstetrics and Gynecology Departmental Molecular Core Facility at the University of Vermont using PrimerSelect (DNASTAR). The quantitative PCR primers for the rat transcripts were: LOX-1 (f):—GATGATCTGAACTTCGTCTTACAAGC—(SEQ ID NO. 1) and (r):—TCAGCAAACACAACTCCTCCTT—(SEQ ID NO. 2); and the housekeeping genes Hprt1 (f):—CTCATGGACTGTTATGGACAGGAC—(SEQ ID NO. 3) and (r):—GCAGGTCAGCAAAGAACTTATAGCC—; (SEQ ID NO. 4) Ywhaz (f):—GATGAAGCCATTGCTGAACTTG—(SEQ ID NO. 5) and (r):—GTCTCCTTGGGTATCCGATGTC—(SEQ ID NO. 6). One microliter of cDNA was used per reaction with 150 nM of the forward and reverse primers and 12.5 µl of Power Sybrgreen Master mix (Life Technologies) in a 25 µl reaction. The reactions were performed using an initial denaturation of 3 minutes at 95° C., 40 cycles of 15 seconds at 95° C. and 60 seconds at 60° C., followed by a melt curve analysis to ensure only the correct product was amplified. One set of PCR products for each gene were checked for correct size on a 2% Agarose gel. Each sample was run in triplicate on the ABI 7000 Sequence Detection System (ABI). For each primer set in the real time PCR reaction, negative water controls were performed to ensure no contamination in the reagents as well as no secondary primer structures were amplified. The LOX-1 primer was designed to span an exon-exon junction to make sure that genomic DNA was not amplified.

Drugs and solutions. HEPES physiological salt solution was made fresh daily and consisted of (mmol/L): 142.00 NaCl, 4.70 KCl, 1.71 MgSO4, 0.50 EDTA, 2.80 CaCl2, 10.00.

HEPES, 1.20 KH2PO4, and 5.00 dextrose. FeTMPyP was purchased from Calbiochem, (Gibbstown, N.J., USA; 341501). LOX-1 antibody was purchased from R&D systems R&D systems (Minneapolis, Minn., USA; AF1564). OxLDL was purchased from Kalen Biomedical (LLC, Montgomerey Village, Minn., USA; 770252-7).

Statistical analysis. Data are presented as mean±standard error of the mean. Analyses were performed by one-way ANOVA with a post-hoc Student Newman Keuls test for multiple comparisons where appropriate or with a Student's T-test. Differences were considered statistical significant at $P<0.05$.

RESULTS

Example 1

Examining Patient Characteristics

There were no significant differences between the 4 groups of women with respect to age or BMI. Blood pressure measured before 20 weeks of gestation was similar in all pregnant groups and was comparable to the blood pressure measured in the group of women who had never been pregnant (NonP). At time of delivery, blood pressure measured in women with an uncomplicated pregnancy (normal pregnant; NP) had not changed compared to the blood pressure measured before 20 weeks of gestation. However, blood pressure measured at delivery from both preeclamptic groups was significantly higher compared to their blood pressure measured before 20 weeks of gestation. Blood pressure was not significantly different between EPE and LPE women. The gestational age of delivery was significantly higher for the NP women compared to both of the preeclamptic groups. The gestational age of delivery was also significant lower in EPE women compared to the LPE women. Lastly, the birth weight of the infants born was significantly different between the 3 pregnant groups with the EPE women having babies with the lowest birth weight and the lowest birth weight percentile compared to the other groups of pregnant women (summarized in Table 1).

TABLE 1

|  | NonP (n = 9) | NP (n = 12) | LPE (n = 10) | EPE (n = 5) |
| --- | --- | --- | --- | --- |
| Age(yrs) | 25.4 (±4.6) | 26 (±4.5) | 31 (±3.6) | 25 (±5) |
| BMI | 24.0 (±3.2) | 26.4 (±3.7) | 26.5 (±7.4) | 24.3 (±3.0) |
| GA sample (wks) | — | 34.9 (±1.8) | 35.8 (±1.6) | 32.3 (±1.6) * |
| GA delivery (wks) | — | 40.1 (±0.93)[#] | 36.0 (±1.4)[^] | 32.5 (±1.4) * |
| BP(sys) < 20 wks | 107 (±6.8) | 110.1 (±7.2) | 119.5 (±12.4) | 122.0 (±5.6) |
| BP (dias) < 20 wks | 65.5 (±5.5) | 66.8 (±3.9) | 73.0 (±7.3) | 73 (±4) |
| BP (sys) delivery | — | 119.4 (±7.3)[#] | 152.40 (±8.59) | 160.0 (±9.5) |
| BP (dias) delivery | — | 68.8 (±11.7) | 91.70 (±6.43) | 100.6 (±11.0) |
| Birthweight (g) | — | 3601 (±380)[#] | 2271.3 (±143.2)[^] | 1462 (±223) * |

* $P < 0.05$ vs NP and LPE.
[#] $P < 0.05$ vs LPE and EPE.
[^] $P < 0.05$ vs NP and EPE.
Abbreviations: NonP = nonpregnant; NP = normal pregnant; LPE = late-onset preeclampsia; EPE = early-onset preeclampsia

TABLE 2

|  | LP-CTL (n = 8) | LP-HC (n = 8) |
|---|---|---|
| Weight (grams) | 408 (±6) | 403 (±10) |
| BP (day 13 diet; mmHg) | 97 (±2) | 104 (±2) * |
| Pups (#) | 16 (0.5) | 12 (±0.6) * |
| Resorptions (#) | 0.7 (±0.2) | 1.4 (±0.4) |
| Avg weight pups (grams) | 2.42 (±0.06) | 2.12 (±0.04) * |
| Avg weight placenta (grams) | 0.44 (±0.01) | 0.48 (±0.01) * |

* $P < 0.05$ vs LP-CTL
Abbreviations: LP-CTL = late-pregnant control rats; LP-HC = late-pregnant high cholesterol treated rats Example 2

The Effect of Circulating Factors in Plasma from EPE Women on BBB Permeability

Figure 2:
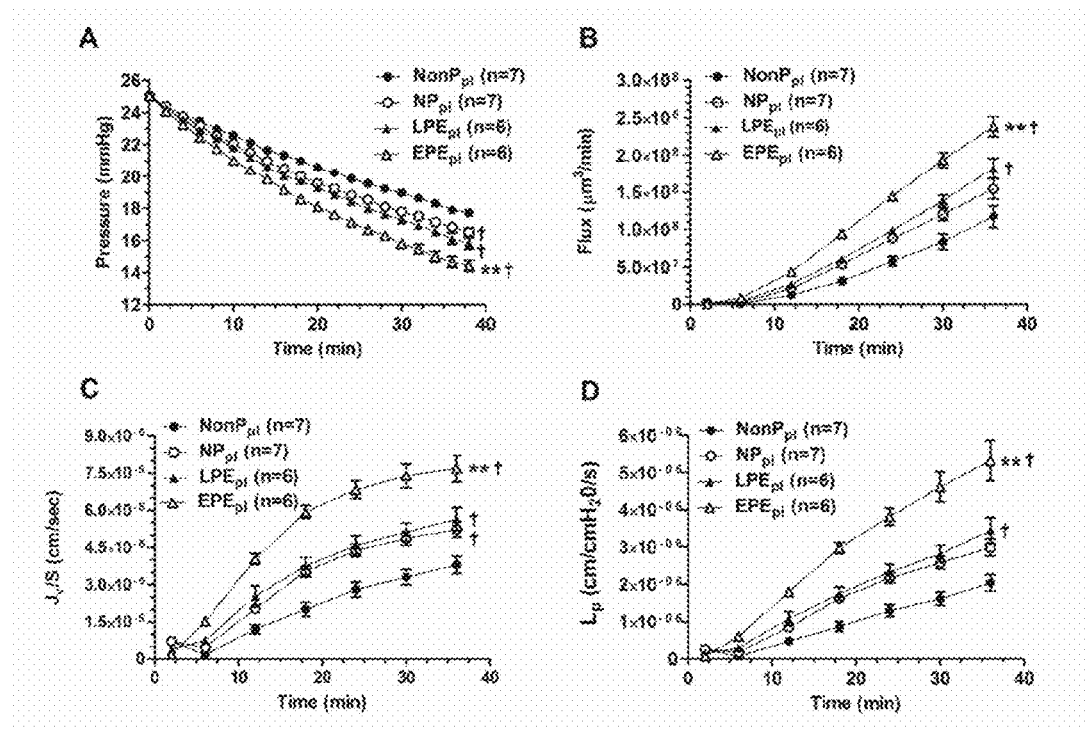
FIG. 2A-2D are sets of graphs depicting the effect of plasma from nonpregnant (NonP), normal pregnant (NP), late-onset preeclamptic (LPE) and early onset (EPE) women on blood brain bather (BBB) permeability. Graphs show: (A) intravascular pressure drop, (B) volume flux, (C) intravascular filtration (Jv/s), and (D) hydraulic conductivity ($L_p$) as a measure of BBB permeability of cerebral veins of NonP rats in response to plasma from EPE, LPE, NP and NonP women. Plasma from EPE and LPE women significantly increased BBB permeability compared to NonP women. Plasma from EPE women significantly increased BBB permeability compared to all other groups, including LPE women. (†$P<0.01$ vs. NonP; **$P<0.01$ vs. all; NonP=nonpregnant; NP=normal pregnant; LPE=late-onset preeclampsia; EPE=early-onset preeclampsia)

It was determined whether circulating factors in plasma from EPE women have different effects on BBB permeability in cerebral veins compared to plasma from LPE women. Here 20% v/v plasma was perfused from LPE and EPE women in a cerebral vein from NonP rats and several parameters were measured including flux and Jv/s to determine $L_p$. Plasma from NonP and NP women were used as controls. The decrease in intravascular pressure due to filtration in response to plasma from EPE, LPE, NP and NonP women was significantly greater in all pregnant groups compared to NonP women (FIG. 2A). Importantly, the decrease in intravascular pressure was significantly greater in EPE women compared to all other groups. After converting the intravascular pressure drop into actual volume flux across the vessel wall (FIG. 2B), plasma from both LPE and EPE showed a significantly increase in flux compared to plasma from NonP women. However, plasma from EPE women caused a significantly higher flux compared NonP, NP and LPE women. After normalizing volume flux to surface area and oncotic pressure of the plasma perfusate (FIGS. 2C-D), plasma from both LPE and EPE women still significantly increased BBB permeability compared to plasma from NonP women. Also, circulating factors in plasma from EPE women significantly increased Jv/S and $L_p$ and thereby increased BBB permeability compared to all other groups, including LPE women. Thus, plasma from EPE women caused a greater increase in BBB permeability compared to plasma from LPE women that may underlie neurological complications.

Example 3

Figure 3:
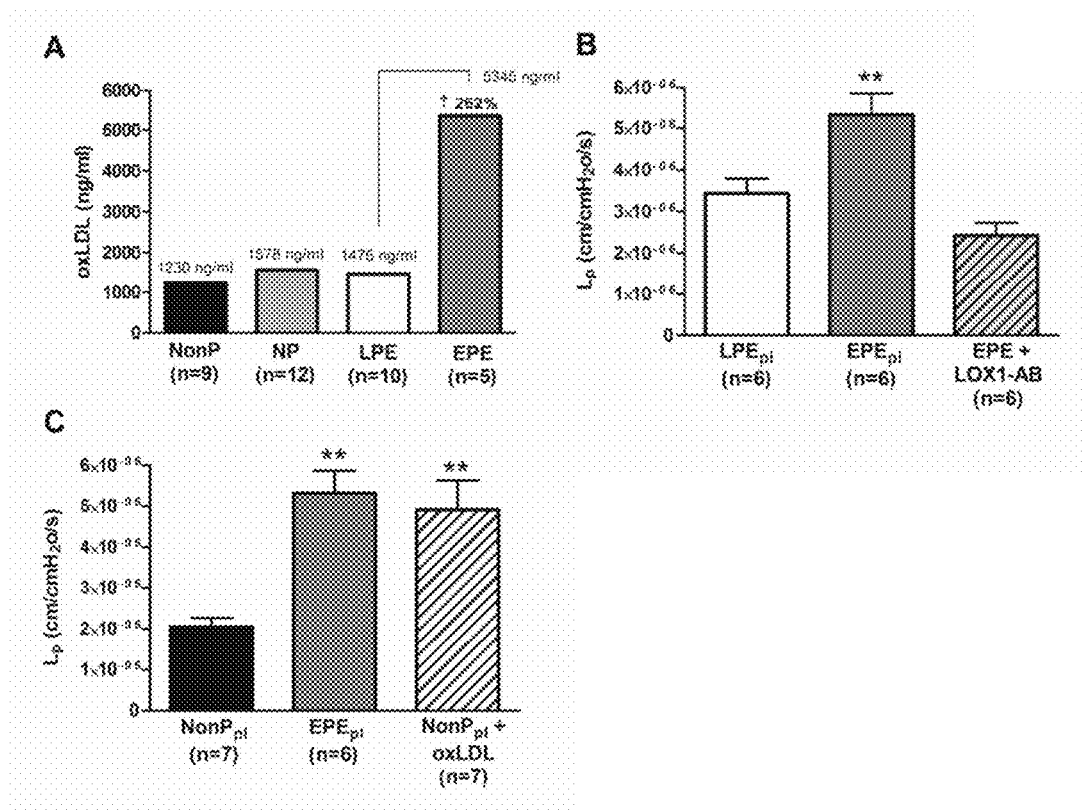
FIG. 3A is a set of graphs demonstrating the presence of oxLDL in EPE and its effect on BBB permeability.
FIG. 3B shows a graph of hydraulic conductivity ($L_p$) at 36 minutes as a measure of BBB permeability in cerebral veins from NonP rats in response to plasma from LPE women and plasma from EPE women with or without the addition of 10 µg/ml LOX-1 antibody. The LOX-1 antibody inhibited the increased BBB permeability induced by plasma from EPE women.
FIG. 3C shows a graph of $L_p$ as a measure of BBB permeability in cerebral veins from NonP rats in response to plasma from NonP and EPE women and plasma from NonP women with addition of 3.5 µg/ml exogenous oxLDL. Exogenous oxLDL significantly increased BBB permeability to the same levels as plasma from EPE women. (**$P<0.01$ vs. all; NonP=nonpregnant; NP=normal pregnant; LPE=late-onset preeclampsia; EPE=early-onset preeclampsia).

The Involvement of oxLDL and LOX-1 Activation in Increased BBB Permeability in EPE Plasma To determine if oxLDL levels are increased in EPE women that could be involved in BBB disruption, oxLDL levels were measured from the plasma of all 4 groups of women. Plasma from EPE women had a 260% increase in oxLDL levels compared to plasma from LPE women (FIG. 3A). The level of oxLDL in plasma from NonP, NP and LPE women were comparable. Thus, a significant increase in the amount to oxLDL in plasma from EPE vs. LPE women.

OxLDL binds its receptor LOX-1 that, once activated, causes endothelial dysfunction in many pathological states such as atherosclerosis, diabetes and hypertension (19, 20). To determine if LOX-1 activation is involved in increasing BBB permeability in cerebral veins in response to plasma from EPE women, LOX-1 was neutralized and $L_p$ then determined. Since Lp is a critical parameter of BBB permeability, only $L_p$ at 36 minutes is in the subsequent figures as a bar chart. Adding a neutralizing LOX-1 antibody in the plasma from EPE women before perfusion in the vein of Galen abolished the increased BBB permeability induced by circulating factors in this plasma (FIG. 3B). Thus, LOX-1 activation is involved in increasing BBB permeability in plasma from EPE women.

Example 4

Effect of oxLDL on BBB Permeability

Next, to determine if oxLDL is able to increase BBB permeability without the presence of other circulating factors present in the plasma from EPE women, 3.5 µg/ml of purified oxLDL was added to plasma from NonP women before perfusing the plasma in cerebral veins. This concentration was used based on the values in the EPE plasma measured by ELISA. Importantly, addition of exogenous oxLDL to plasma from NonP women caused a significant increase in BBB permeability that was comparable to plasma from women with EPE (FIG. 3C). Thus, these data suggest that high levels of oxLDL in plasma from EPE women increase BBB permeability through LOX-1 activation.

Example 5

Effect of FeTMPyP on oxLDL-LOX-1 Induced BBB Permeability in EPE Plasma

Figure 4:
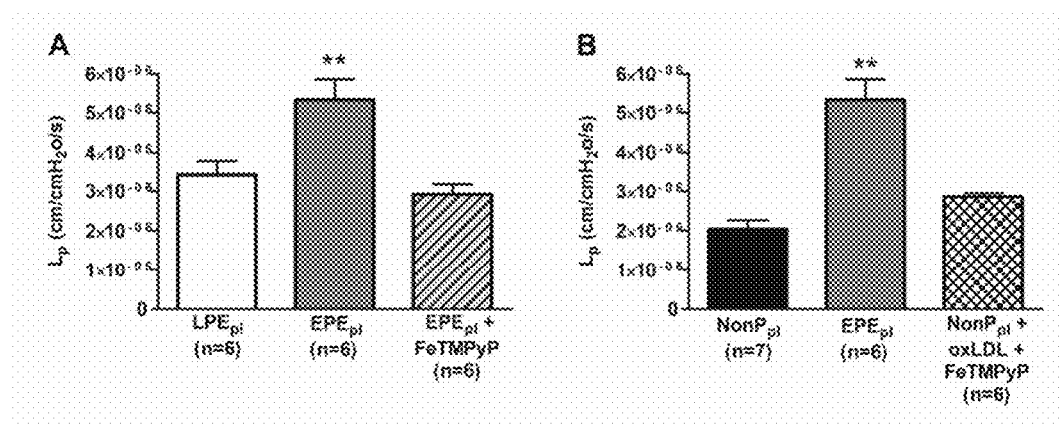
FIGS. 4A and 4B are sets of graphs showing the effect of the peroxynitrite scavenger FeTMPyP on BBB permeability in EPE induced by oxLDL.

Activation of LOX-1 leads to increased production of superoxide through NADPH-oxidase that rapidly binds NO to form $ONOO^-$ (25). Previous studies confirmed generation of $ONOO^-$ in the placental and maternal systemic vasculature of preeclamptic women, however, involvement of $ONOO^-$ generation in response to LOX-1 activation in disrupting the BBB is not known (29, 31). Cerebral veins from NonP rats were perfused with plasma from EPE women plus 50 µM FeTMPyP, a selective $ONOO^-$ decomposition catalyst. FeTMPyP significantly inhibited BBB permeability caused by plasma from EPE women (FIG. 4A), demonstrating that $ONOO^-$ generation is also involved in BBB disruption in cerebral veins after exposure to plasma from EPE women.

Example 6

Effect of Exogenous oxLDL on BBB

To determine that the increase in BBB permeability caused by exogenous oxLDL (FIG. 3C) was due to increased generation of $ONOO^-$, 50 µM FeTMPyP was added to the plasma from NonP women plus oxLDL. Addition of FeTMPyP inhibited BBB permeability induced by oxLDL (FIG. 4B), demonstrating that $ONOO^-$ generation is induced by oxLDL and leads to BBB disruption.

Example 7

Effects of Pathologically High Lipids on Blood Pressure, Pregnancy Outcome, BBB Permeability and LOX-1 mRNA Expression in a Pregnant High-Cholesterol Rat Model Because increased levels of cholesterol are present in preeclampsia (14-16) and increased oxLDL is involved in disrupting the BBB in EPE, it was important to determine the effect of pathologically high levels of cholesterol in pregnancy on pregnancy outcome and BBB permeability using a rat model. Rats treated with high-cholesterol for 14 days had a 350% increase in cholesterol compared to LP-CTL animals. Table 1 shows characteristics and pregnancy outcome in these rats. LP-HC rats had modest, but significantly higher blood pressures vs. LP-CTL rats. Further, LP-HC rats carried a significantly smaller number of pups, and had a higher rate of reabsorptions. Pup weights from the LP-HC rats were significantly lower, similar to EPE, with a significant increase in placental weight.

Example 8

Effect of Pathologically High Cholesterol in Pregnant Rats on BBB Permeability

Figure 5:
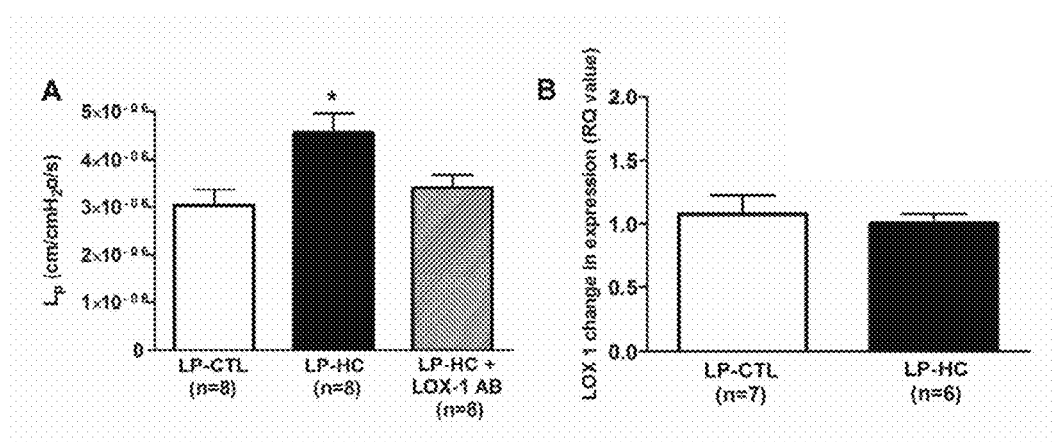
FIGS. 5A and 5B are sets of graphs showing the effects of pathologically high levels of cholesterol in pregnant rats.

To determine if pathologically high levels of cholesterol in pregnant rats increased BBB permeability, cerebral veins from LP-HC or LP-CTL rats were perfused with 20% v/v plasma from the same animal and measured $L_p$. BBB permeability in cerebral veins from LP-HC animals was significantly increased compared to the LP-CTL animals (FIG. 5A). To determine if LOX-1 activation was involved in increasing BBB permeability in LP-HC animals, a neutralizing LOX-1 antibody was added to the plasma from LP-HC rats before perfusing in the cerebral veins. Addition of the LOX-1 antibody abolished the increased BBB permeability in LP-HC animals (FIG. 5A); suggesting oxLDL was involved in increasing BBB permeability in the LP-HC animals, similar as in EPE.

Example 9

LOX-1 mRNA Expression Levels in Cerebral Vasculature as an Independent Factor of BBB Permeability Lastly, to determine if LOX-1 mRNA expression was increased in the cerebral vasculature of LP-HC animals that may increase BBB permeability independent of increased oxLDL, we isolated the MCAs from the same animals as used for the permeability experiments to determine mRNA expression of LOX-1. mRNA expression of LOX-1 was similar in the LP-HC and LP-CTL animals (FIG. 5B), suggesting that circulating oxLDL is activating LOX-1 to increase BBB permeability as opposed to upregulation of LOX-1.

REFERENCES

1. Duley, L. 2009. The global impact of pre-eclampsia and eclampsia. *Semin Perinatol* 33:130-137.
2. Zeeman, G. G. 2009. Neurologic complications of pre-eclampsia. *Semin Perinatol* 33:166-172.
3. Okanloma, K. A., and Moodley, J. 2000. Neurological complications associated with the pre-eclampsia/eclampsia syndrome. *Int J Gynaecol Obstet* 71:223-225.
4. Ogge, G., Chaiworapongsa, T., Romero, R., Hussein, Y., Kusanovic, J. P., Yeo, L., Kim, C. J., and Hassan, S. S. 2011. Placental lesions associated with maternal underperfusion are more frequent in early-onset than in late-onset preeclampsia. *J Perinat Med* 39:641-652.
5. Douglas, K. A., and Redman, C. W. 1994. Eclampsia in the United Kingdom. *BMJ* 309:1395-1400.
6. Douglas, K. A., and Redman, C. W. 1992. Eclampsia in the United Kingdom. The 'BEST' way forward. *Br J Obstet Gynaecol* 99:355-356.
7. von Dadelszen, P., Magee, L. A., and Roberts, J. M. 2003. Subclassification of preeclampsia. *Hypertens Pregnancy* 22:143-148.
8. Cipolla, M. J. 2007. Cerebrovascular function in pregnancy and eclampsia. *Hypertension* 50:14-24.
9. Zeeman, G. G., Hatab, M., and Twickler, D. M. 2003. Maternal cerebral blood flow changes in pregnancy. *Am J Obstet Gynecol* 189:968-972.
10. Friedman, A., Kaufer, D., and Heinemann, U. 2009. Blood-brain barrier breakdown-inducing astrocytic transformation: novel targets for the prevention of epilepsy. *Epilepsy Res* 85:142-149.
11. Abbott, N. J., Ronnback, L., and Hansson, E. 2006. Astrocyte-endothelial interactions at the blood-brain barrier. *Nat Rev Neurosci* 7:41-53.
12. Euser, A. G., and Cipolla, M. J. 2007. Cerebral blood flow autoregulation and edema formation during pregnancy in anesthetized rats. *Hypertension* 49:334-340.
13. Amburgey, O. A., Chapman, A. C., May, V., Bernstein, I. M., and Cipolla, M. J. 2010. Plasma from preeclamptic women increases blood-brain barrier permeability: role of vascular endothelial growth factor signaling. *Hypertension* 56:1003-1008.
14. Hubel, C. A., Lyall, F., Weissfeld, L., Gandley, R. E., and Roberts, J. M. 1998. Small low-density lipoproteins and vascular cell adhesion molecule-1 are increased in association with hyperlipidemia in preeclampsia. *Metabolism* 47:1281-1288.
15. Belo, L., Caslake, M., Gaffney, D., Santos-Silva, A., Pereira-Leite, L., Quintanilha, A., and Rebelo, I. 2002. Changes in LDL size and HDL concentration in normal and preeclamptic pregnancies. *Atherosclerosis* 162:425-432.
16. Enquobahrie, D. A., Williams, M. A., Butler, C. L., Frederick, I. O., Miller, R. S., and Luthy, D. A. 2004. Maternal plasma lipid concentrations in early pregnancy and risk of preeclampsia. *Am J Hypertens* 17:574-581.
17. Redman, C. W., and Sargent, I. L. 2005. Latest advances in understanding preeclampsia. *Science* 308:1592-1594.
18. Buhimschi, I. A., Saade, G. R., Chwalisz, K., and Garfield, R. E. 1998. The nitric oxide pathway in preeclampsia: pathophysiological implications. *Hum Reprod Update* 4:25-42.
19. Ogura, S., Kakino, A., Sato, Y., Fujita, Y., Iwamoto, S., Otsui, K., Yoshimoto, R., and Sawamura, T. 2009. Lox-1: the multifunctional receptor underlying cardiovascular dysfunction. *Circ J* 73:1993-1999.
20. Chen, M., Masaki, T., and Sawamura, T. 2002. LOX-1, the receptor for oxidized low-density lipoprotein identified from endothelial cells: implications in endothelial dysfunction and atherosclerosis. *Pharmacol Ther* 95:89-100.
21. Qiu, C., Phung, T. T., Vadachkoria, S., Muy-Rivera, M., Sanchez, S. E., and Williams, M. A. 2006. Oxidized low-density lipoprotein (Oxidized LDL) and the risk of preeclampsia. *Physiol Res* 55:491-500.
22. Morton, J. S., Abdalvand, A., Jiang, Y., Sawamura, T., Uwiera, R. R., and Davidge, S. T. 2012. Lectin-like oxidized low-density lipoprotein 1 receptor in a reduced uteroplacental perfusion pressure rat model of preeclampsia. *Hypertension* 59:1014-1020.
23. Sankaralingam, S., Xu, Y., Sawamura, T., and Davidge, S. T. 2009. Increased lectin-like oxidized low-density 24. Sanchez, S. E., Williams, M. A., Muy-Rivera, M., Qiu, C., Vadachkoria, S., and Bazul, V. 2005. A case-control study of oxidized low density lipoproteins and preeclampsia risk. *Gynecol Endocrinol* 21:193-199.

25. Cominacini, L., Rigoni, A., Pasini, A. F., Garbin, U., Davoli, A., Campagnola, M., Pastorino, A. M., Lo Cascio, V., and Sawamura, T. 2001. The binding of oxidized low density lipoprotein (ox-LDL) to ox-LDL receptor-1 reduces the intracellular concentration of nitric oxide in endothelial cells through an increased production of superoxide. *J Biol Chem* 276:13750-13755.

26. Chen, X. P., Xun, K. L., Wu, Q., Zhang, T. T., Shi, J. S., and Du, G. H. 2007. Oxidized low density lipoprotein receptor-1 mediates oxidized low density lipoprotein-induced apoptosis in human umbilical vein endothelial cells: role of reactive oxygen species. *Vascul Pharmacol* 47:1-9.

27. Beckman, J. S., and Koppenol, W. H. 1996. Nitric oxide, superoxide, and peroxynitrite: the good, the bad, and ugly. *Am J Physiol* 271:C1424-1437.

28. Sandau, K., Pfeilschifter, J., and Brune, B. 1997. The balance between nitric oxide and superoxide determines apoptotic and necrotic death of rat mesangial cells. *J Immunol* 158:4938-4946.

29. Roggensack, A. M., Zhang, Y., and Davidge, S. T. 1999. Evidence for peroxynitrite formation in the vasculature of women with preeclampsia. *Hypertension* 33:83-89.

30. Lin, Y. L., Chang, H. C., Chen, T. L., Chang, J. H., Chiu, W. T., Lin, J. W., and Chen, R. M. 2010. Resveratrol protects against oxidized LDL-induced breakage of the blood-brain bather by lessening disruption of tight junctions and apoptotic insults to mouse cerebrovascular endothelial cells. *J Nutr* 140:2187-2192.

31. Myatt, L., and Webster, R. P. 2009. Vascular biology of preeclampsia. *J Thromb Haemost* 7:375-384.

32. Neal, C. R., Hunter, A. J., Harper, S. J., Soothill, P. W., and Bates, D. O. 2004. Plasma from women with severe pre-eclampsia increases microvascular permeability in an animal model in vivo. *Clin Sci (Lond)* 107:399-405.

33. Wikstrom, A. K., Nash, P., Eriksson, U. J., and Olovsson, M. H. 2009. Evidence of increased oxidative stress and a change in the plasminogen activator inhibitor (PAI)-1 to PAI-2 ratio in early-onset but not late-onset preeclampsia. *Am J Obstet Gynecol* 201:597 e591-598.

34. Egbor, M., Ansari, T., Morris, N., Green, C. J., and Sibbons, P. D. 2006. Morphometric placental villous and vascular abnormalities in early- and late-onset pre-eclampsia with and without fetal growth restriction. *BJOG* 113:580-589.

35. Kim, Y. J., Park, H., Lee, H. Y., Ahn, Y. M., Ha, E. H., Suh, S. H., and Pang, M. G. 2007. Paraoxonase gene polymorphism, serum lipid, and oxidized low-density lipoprotein in preeclampsia. *Eur J Obstet Gynecol Reprod Biol* 133:47-52.

36. Uzun, H., Benian, A., Madazli, R., Topcuoglu, M. A., Aydin, S., and Albayrak, M. 2005. Circulating oxidized low-density lipoprotein and paraoxonase activity in preeclampsia. *Gynecol Obstet Invest* 60:195-200.

37. Branch, D. W., Mitchell, M. D., Miller, E., Palinski, W., and Witztum, J. L. 1994. Pre-eclampsia and serum antibodies to oxidised low-density lipoprotein. *Lancet* 343: 645-646.

38. Reyes, L. M., Garcia, R. G., Ruiz, S. L., Broadhurst, D., Aroca, G., Davidge, S. T., and Lopez-Jaramillo, P. 2012. Angiogenic imbalance and plasma lipid alterations in women with preeclampsia from a developing country. *Growth Factors* 30:158-166.

39. Pecks, U., Caspers, R., Schiessl, B., Bauerschlag, D., Piroth, D., Maass, N., and Rath, W. 2012. The evaluation of the oxidative state of low-density lipoproteins in intrauterine growth restriction and preeclampsia. *Hypertens Pregnancy* 31:156-165.

40. Ross, R. 1993. The pathogenesis of atherosclerosis: a perspective for the 1990s. *Nature* 362:801-809.

41. Staff, A. C., Dechend, R., and Pijnenborg, R. 2010. Learning from the placenta: acute atherosis and vascular remodeling in preeclampsia-novel aspects for atherosclerosis and future cardiovascular health. *Hypertension* 56:1026-1034.

42. Lee, H., Park, H., Kim, Y. J., Kim, H. J., Ahn, Y. M., Park, B., Park, J. H., and Lee, B. E. 2005. Expression of lectin-like oxidized low-density lipoprotein receptor-1 (LOX-1) in human preeclamptic placenta: possible implications in the process of trophoblast apoptosis. *Placenta* 26:226-233.

43. Nakano, A., Inoue, N., Sato, Y., Nishimichi, N., Takikawa, K., Fujita, Y., Kakino, A., Otsui, K., Yamaguchi, S., Matsuda, H., et al. 2010. LOX-1 mediates vascular lipid retention under hypertensive state. *J Hypertens* 28:1273-1280.

44. Mitra, S., Goyal, T., and Mehta, J. L. 2011. Oxidized LDL, LOX-1 and atherosclerosis. *Cardiovasc Drugs Ther* 25:419-429.

45. Heeba, G., Hassan, M. K., Khalifa, M., and Malinski, T. 2007. Adverse balance of nitric oxide/peroxynitrite in the dysfunctional endothelium can be reversed by statins. *J Cardiovasc Pharmacol* 50:391-398.

46. Miller, A. A., Drummond, G. R., De Silva, T. M., Mast, A. E., Hickey, H., Williams, J. P., Broughton, B. R., and Sobey, C. G. 2009. NADPH oxidase activity is higher in cerebral versus systemic arteries of four animal species: role of Nox2. *Am J Physiol Heart Circ Physiol* 296:H220-225.

47. Kroll, J., and Waltenberger, J. 1999. A novel function of VEGF receptor-2 (KDR): rapid release of nitric oxide in response to VEGF-A stimulation in endothelial cells. *Biochem Biophys Res Commun* 265:636-639.

48. Loureiro, R., Leite, C. C., Kahhale, S., Freire, S., Sousa, B., Cardoso, E. F., Alves, E. A., Borba, P., Cerri, G. G., and Zugaib, M. 2003. Diffusion imaging may predict reversible brain lesions in eclampsia and severe preeclampsia: initial experience. *Am J Obstet Gynecol* 189: 1350-1355.

49. Marchi, N., Teng, Q., Ghosh, C., Fan, Q., Nguyen, M. T., Desai, N. K., Bawa, H., Rasmussen, P., Masaryk, T. K., and Janigro, D. 2010. Blood-brain barrier damage, but not parenchymal white blood cells, is a hallmark of seizure activity. *Brain Res* 1353:176-186.

50. Fuster, J. J., Castillo, A. I., Zaragoza, C., Ibanez, B., and Andres, V. 2012 Animal models of atherosclerosis. *Prog Mol Biol Transl Sci* 105:1-23.

51. Cipolla, M. J., DeLance, N., and Vitullo, L. 2006. Pregnancy prevents hypertensive remodeling of cerebral arteries: a potential role in the development of eclampsia. *Hypertension* 47:619-626.

52. Roberts, T. J., Chapman, A. C., and Cipolla, M. J. 2009. PPAR-gamma agonist rosiglitazone reverses increased cerebral venous hydraulic conductivity during hypertension. *Am J Physiol Heart Circ Physiol* 297:H1347-1353.

53. Schreurs, M. P., Houston, E. M., May, V., and Cipolla, M. J. 2012. The adaptation of the blood-brain barrier to vascular endothelial growth factor and placental growth factor during pregnancy. *FASEB J* 26:355-362.
54. Cipolla, M. J., Huang, Q., and Sweet, J. G. 2011 Inhibition of protein kinase Cbeta reverses increased blood-brain barrier permeability during hyperglycemic stroke and prevents edema formation in vivo. *Stroke* 42:3252-3257.
55. Mayhan, W. G. 1995. Role of nitric oxide in disruption of the blood-brain barrier during acute hypertension. *Brain Res* 686:99-103.
56. Cuzzocrea, S., Misko, T. P., Costantino, G., Mazzon, E., Micali, A., Caputi, A. P., Macarthur, H., and Salvemini, D. 2000. Beneficial effects of peroxynitrite decomposition catalyst in a rat model of splanchnic artery occlusion and reperfusion. *FASEB J* 14:1061-1072.
57. Xie, Z., Wei, M., Morgan, T. E., Fabrizio, P., Han, D., Finch, C. E., and Longo, V. D. 2002. Peroxynitrite mediates neurotoxicity of amyloid beta-peptide1-42- and lipopolysaccharide-activated microglia. *J Neurosci* 22:3484-3492.
58. Palomares, S. M., Gardner-Morse, I., Sweet, J. G., and Cipolla, M. J. 2012. Peroxynitrite decomposition with FeTMPyP improves plasma-induced vascular dysfunction and infarction during mild but not severe hyperglycemic stroke. *J Cereb Blood Flow Metab.*

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method for identifying a subject at risk of seizure, comprising isolating a tissue sample from a pregnant subject wherein the pregnant subject does not have preeclampsia and wherein blood pressure of the subject is within normal levels, measuring a level of oxLDL in the pregnant subject, wherein the subject is at risk of seizure if the oxLDL levels are greater than a control level, and further comprising administering an anti-seizure prophylaxis to the subject if the levels of oxLDL are greater than a control level.

2. The method of claim 1, wherein the oxLDL levels are greater than 1,600 ng/ml.

3. The method of claim 1, wherein the tissue sample is a blood sample.

4. The method of claim 1, wherein the anti-seizure prophylaxis is magnesium sulfate.

5. The method of claim 1, wherein the levels of oxLDL are measured using an antibody assay.

6. The method of claim 1, wherein the levels of oxLDL are measured using a kit for detecting oxLDL.

7. The method of claim 1, wherein the subject is in the first trimester of pregnancy.

8. The method of claim 1, wherein the subject is in the second trimester of pregnancy.

9. The method of claim 1, wherein the subject is in the third trimester of pregnancy.

10. The method of claim 1, further comprising measuring the cholesterol of the subject.

11. The method of claim 10, wherein the cholesterol of the subject is above normal levels.

* * * * *

SEQUENCE LISTING

```
<160> NUMBER OF SEQ ID NOS: 6

<210> SEQ ID NO 1
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 1
gatgatctga acttcgtctt acaagc                                              26

<210> SEQ ID NO 2
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 2
tcagcaaaca caactcctcc tt                                                  22

<210> SEQ ID NO 3
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 3
ctcatggact gttatggaca ggac                                                24

<210> SEQ ID NO 4
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 4
gcaggtcagc aaagaactta tagcc                                               25

<210> SEQ ID NO 5
<211> LENGTH: 22
<212> TYPE: DNA
<213> ORGANISM: Artificial Sequence
<220> FEATURE:
<223> OTHER INFORMATION: Synthetic oligonucleotide
```

```
<400> SEQUENCE: 5
gatgaagcca ttgctgaact tg                                              22

<210> SEQ ID NO 6
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 6
gtctccttgg gtatccgatg tc                                              22
```